(12) United States Patent
Di Sessa et al.

(10) Patent No.: US 8,277,442 B2
(45) Date of Patent: Oct. 2, 2012

(54) DISPOSABLE TIP APPARATUS FOR LASER SURGICAL DEVICE

(75) Inventors: Alexandre B. Di Sessa, Walnut Creek, CA (US); Mihai I. A. Boitor, Martinez, CA (US)

(73) Assignee: Zila, Inc., Fort Collins, CO (US)

( * ) Notice: Subject to any disclaimer, the term of this patent is extended or adjusted under 35 U.S.C. 154(b) by 1185 days.

(21) Appl. No.: 12/115,336

(22) Filed: May 5, 2008

(65) Prior Publication Data
US 2009/0275930 A1   Nov. 5, 2009

(51) Int. Cl.
*A61B 18/18* (2006.01)
(52) U.S. Cl. .............................................. 606/1; 606/13
(58) Field of Classification Search ................. 606/1–19
See application file for complete search history.

(56) References Cited

U.S. PATENT DOCUMENTS

| | | | |
|---|---|---|---|
| 4,526,170 A * | 7/1985 | Tanner | 606/7 |
| 4,785,805 A * | 11/1988 | Joffe et al. | 606/15 |
| 4,895,145 A * | 1/1990 | Joffe et al. | 606/11 |
| 5,304,172 A | 4/1994 | Manoukian et al. | |
| 5,364,391 A * | 11/1994 | Konwitz | 606/16 |
| 5,464,436 A | 11/1995 | Smith | |
| 5,607,420 A | 3/1997 | Schuman | |
| 5,616,141 A | 4/1997 | Cipolla | |
| 5,927,977 A | 7/1999 | Sale et al. | |
| 5,928,220 A | 7/1999 | Shimoji | |
| 5,951,544 A * | 9/1999 | Konwitz | 606/16 |
| 6,013,096 A | 1/2000 | Tucek | |
| 6,039,565 A | 3/2000 | Chou et al. | |
| 6,059,776 A * | 5/2000 | Gatto | 606/13 |
| 6,099,520 A | 8/2000 | Shimoji | |
| 6,200,332 B1 * | 3/2001 | Del Giglio | 607/89 |
| 6,213,998 B1 | 4/2001 | Shen et al. | |
| 6,231,567 B1 | 5/2001 | Rizoiu et al. | |
| 6,254,597 B1 | 7/2001 | Rizoiu et al. | |
| 6,261,310 B1 | 7/2001 | Neuberger et al. | |
| 6,325,791 B1 | 12/2001 | Shimoji | |
| 6,327,942 B1 | 12/2001 | Mariol et al. | |
| 6,458,120 B1 | 10/2002 | Shen et al. | |
| 6,572,637 B1 | 6/2003 | Yamazaki et al. | |
| 6,574,401 B2 | 6/2003 | Neuberger et al. | |
| 6,746,473 B2 | 6/2004 | Shanks et al. | |
| D496,101 S | 9/2004 | Davison | |
| 6,868,221 B1 | 3/2005 | Wood et al. | |
| 7,033,350 B2 | 4/2006 | Bahk | |
| 7,118,563 B2 | 10/2006 | Weckwerth et al. | |
| 7,137,977 B2 | 11/2006 | Brucker et al. | |
| 7,267,672 B2 | 9/2007 | Altshuler et al. | |
| 7,288,086 B1 | 10/2007 | Andriasyan | |
| 7,290,940 B2 | 11/2007 | Boutoussov | |
| 7,320,594 B1 | 1/2008 | Rizoiu et al. | |
| 7,695,469 B2 * | 4/2010 | Boutoussov et al. | 606/13 |
| 2002/0081080 A1 * | 6/2002 | Balle-Petersen et al. | 385/93 |

(Continued)

FOREIGN PATENT DOCUMENTS

WO    WO 01/10327 A1    2/2001

*Primary Examiner* — Henry M Johnson, III
(74) *Attorney, Agent, or Firm* — Jeffer Mangels; Butler & Mitchell LLP

(57) ABSTRACT

A multi-component sterile, disposable tip apparatus for laser surgical devices is provided and features assembly for alignment of a self-contained optical fiber to the surgical device and releasably locking assembly between the tip and device.

17 Claims, 4 Drawing Sheets

U.S. PATENT DOCUMENTS

2004/0259053 A1 12/2004 Bekov et al.
2006/0064080 A1* 3/2006 Cao .................................. 606/10
2008/0154249 A1* 6/2008 Cao .................................. 606/10
2008/0161783 A1* 7/2008 Cao .................................. 606/10

* cited by examiner

DISPOSABLE TIP APPARATUS FOR LASER SURGICAL DEVICE

CROSS-REFERENCES TO RELATED APPLICATIONS

None.

STATEMENT REGARDING FEDERALLY SPONSORED RESEARCH OR DEVELOPMENT

None.

REFERENCE TO A MICRO-FICHE APPENDIX

None.

BACKGROUND OF THE INVENTION

This invention relates to surgical instruments for laser ablation procedures. More particularly, the invention relates to a sterile, disposable tip apparatus for such surgical instruments.

BRIEF SUMMARY OF THE INVENTION

Medical laser treatment using hand-held instruments has generally been developed for ophthalmic, dental, orthopedic, and similar surgical procedures where the treatment area is confined or particularly difficult to reach. Typically, laser light is transmitted from a laser source though an optical fiber to a treatment site. The optical fiber terminates proximally in a laser source connector for connection to the laser source and terminates distally in a handpiece manipulated by the surgeon.

A handpiece used during one procedure cannot be used with another patient in a subsequent procedure unless some form of sterilization is performed. Types of sterilization techniques range from autoclaves to gas. Gas procedures are time consuming and costly. Autoclave temperatures generally have proven too severe for laser surgical handpieces to withstand.

Accordingly it would be useful to provide a sterile, disposable tip for use with a laser surgical device.

It would be of further use if the sterile, disposable tip provided means for precise alignment of the optical fiber in the tip to the source of laser energy in the surgical device.

Yet another useful advantage would be for the sterile, disposable tip to be releasably attached to the device with precise optical, mechanical, magnetic, electromechanical, or electromagnetic locking and alignment assembly.

Other features, advantages, and objects of the present invention will become apparent with reference to the following description and accompanying drawings.

DETAILED DESCRIPTION OF THE INVENTION

Figure 1:
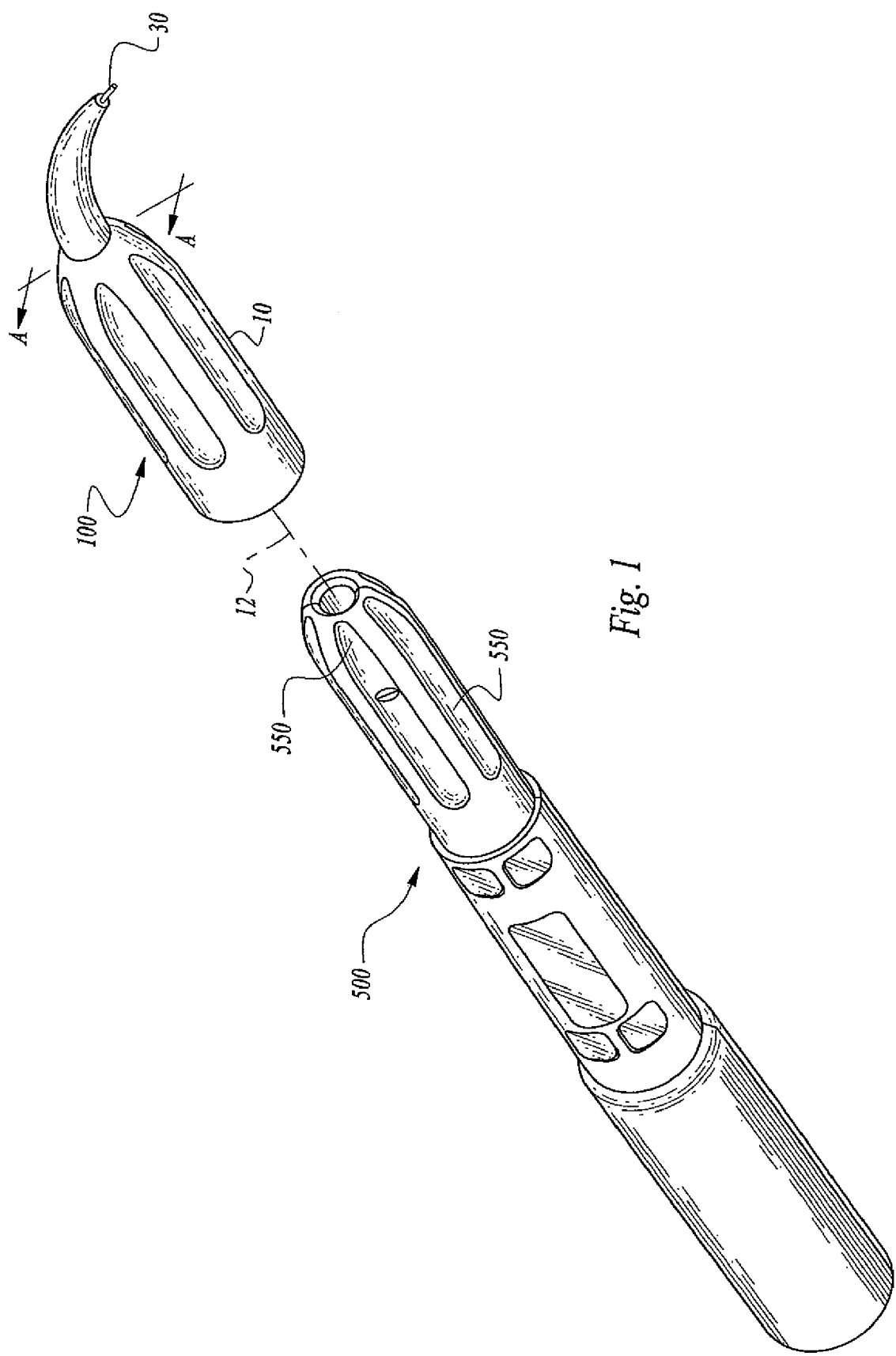
FIG. 1 is a perspective view of an embodiment of disposable tip apparatus 100 adapted to reusable laser surgical device 500.

With reference to drawing FIGS. 1-4, disposable tip apparatus 100 for reusable laser surgical device is presented.

The tip apparatus 100 comprises in combination: a first end 10 having a longitudinal axis 12 and adapted to releasably fit on the distal end of the surgical device 500; second end 20 tapering to a discharge tip 22; optical fiber means 30 for delivery of light energy axially positioned within the tip apparatus from within the first end 10 and extending beyond the discharge tip 22; means for removably locking the first end 10 to the surgical device 500 and connecting the first end 10, second end 20, and optical fiber means 30; and means for aligning fiber optic means 30 within the tip apparatus 10 with the surgical device 500 for surgical laser treatment.

An embodiment of the tip apparatus 100 provides means for aligning the optical fiber means within the tip apparatus with the surgical device comprising a sleeve on the tip first end.

Another embodiment of tip apparatus 100 provides means for aligning the optical fiber means within the tip apparatus with the surgical device comprises at least two slits 550 spaced equally apart on the distal end of the surgical device 500 and a tip first end sleeve 16 having internal longitudinal ribs 18 adapted to fit the surgical device slits 550. In this manner, the tip apparatus 100 is secured to the surgical device 500 in such a way as to allow freedom of movement in only one dimension, along the longitudinal axis 12.

An embodiment of the tip apparatus 100 provides a discharge tip end is along (not shown) the first end longitudinal axis 12.

Figure 2:
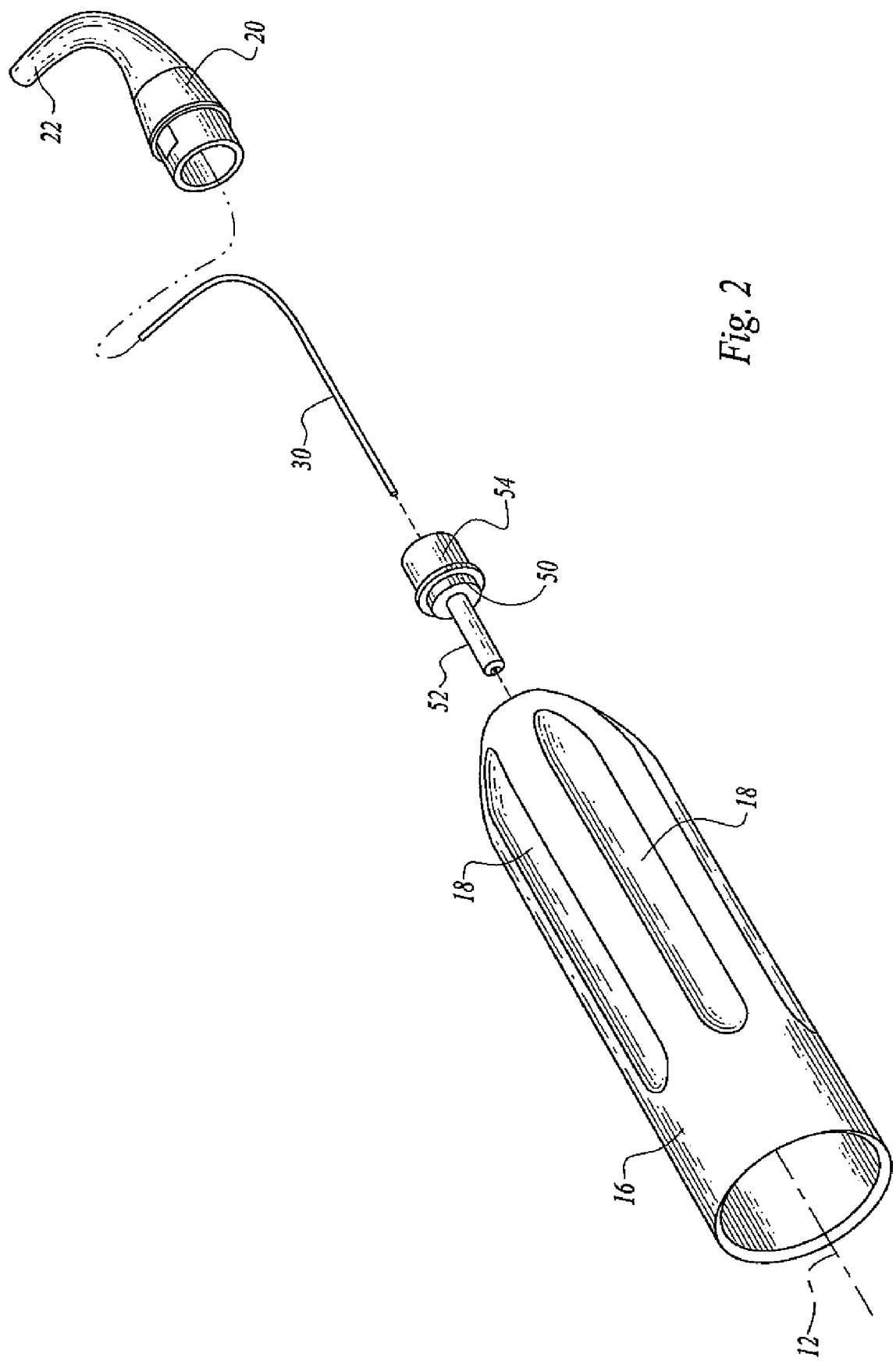
FIG. 2 is an exploded perspective view of the embodiment of disposable tip apparatus 100 of FIG. 1.
Figure 3:
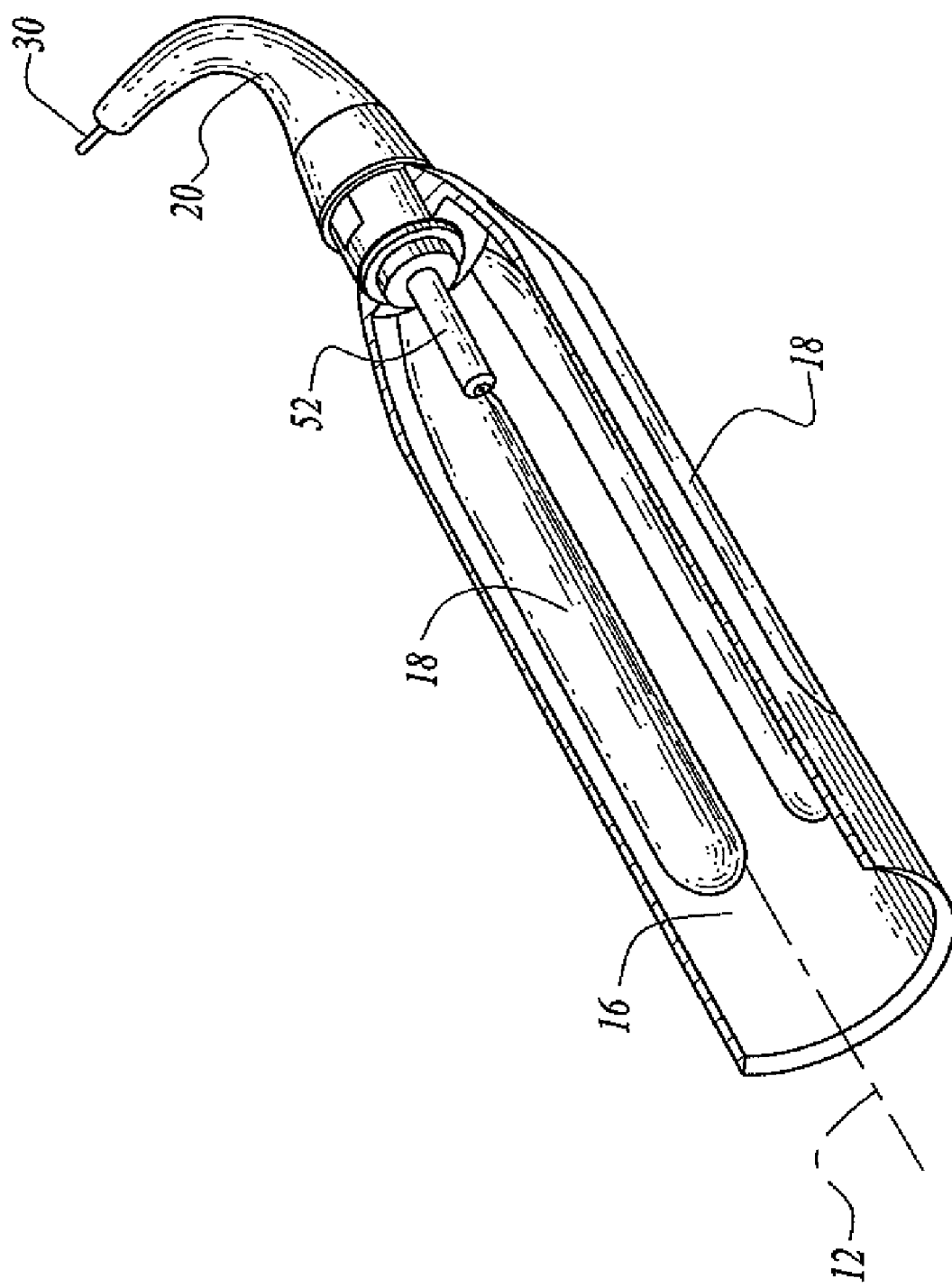
FIG. 3 is a cross sectional view of the embodiment of disposable tip apparatus 100 of FIG. 1 taken at "A-A."
Figure 4:
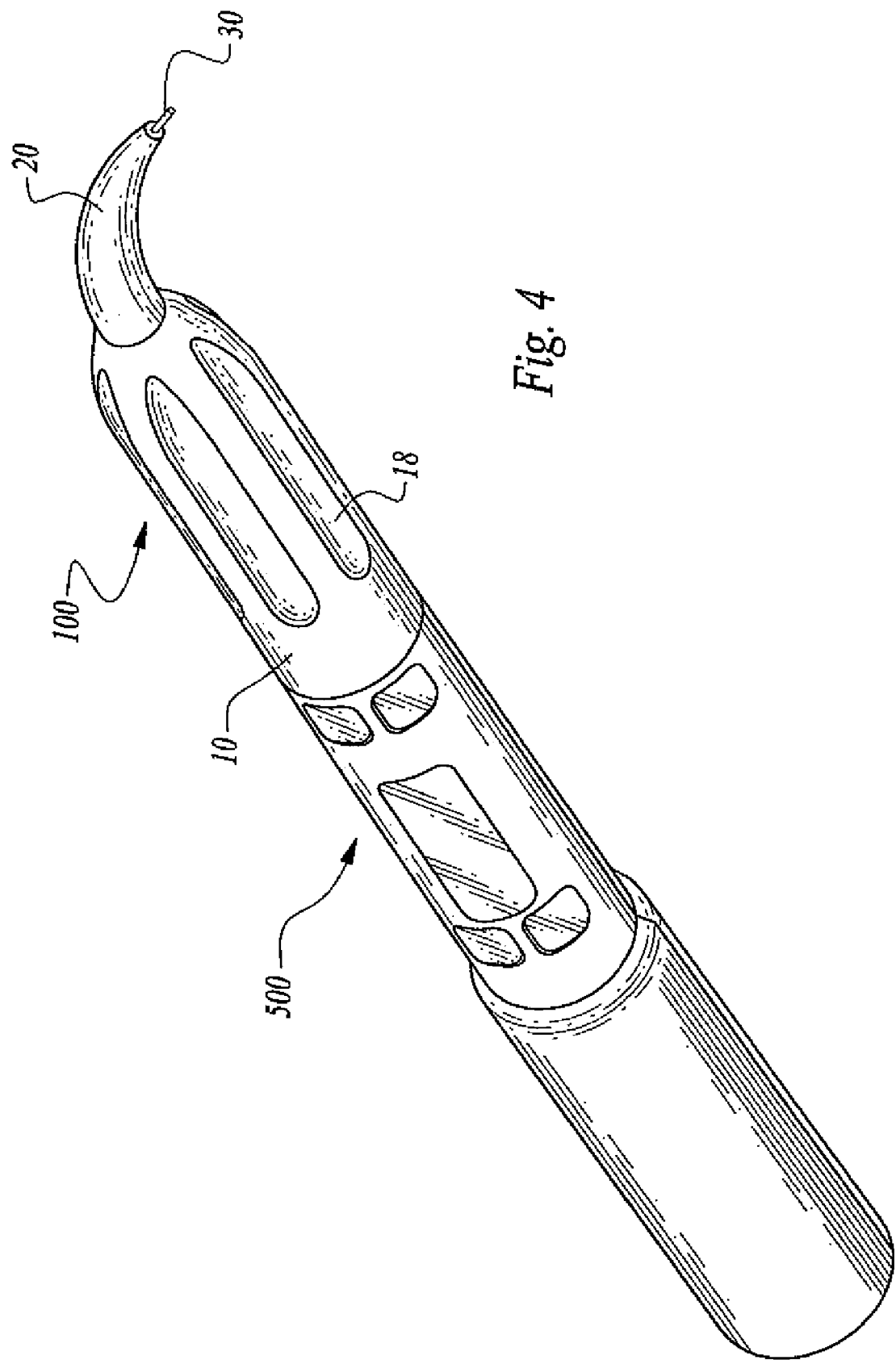
FIG. 4 is a perspective view of disposable tip apparatus 100 of FIG. 1 engaged with a reusable laser surgical device 500.

Another embodiment of tip apparatus 100 provides the discharge tip 22 end at an acute angle to the first end 10 longitudinal axis 12, FIGS. 1-3.

Yet another embodiment of tip apparatus 100 provides the discharge tip 22 end at a right angle (not shown) to the first end longitudinal axis 12.

As depicted in FIGS. 2 and 3 the first end 10, second end 20, and fiber optic means 30 communicate via a common connector 50 comprising a probe 52 and housing 54 adapted to the second end 20. The probe 52 and housing 54 further comprise an axial orifice size to receive and contain fiber optic means 30.

The probe 52 and housing 54 further comprise means for releasably locking the first end 10 to the surgical device 500 comprises at least one member of the group consisting of means for magnetic coupling, means for mechanical coupling, means for electromechanical coupling, and means for electromagnetic coupling. The preferred embodiment of tip apparatus 100 comprises magnetic material in the housing 54 which, when the tip apparatus 100 is positioned on the surgical device 500, is proximate to a magnet within the surgical device 500, releasably locking the tip apparatus 100 to the surgical device 500.

The tip apparatus 100 first end 10 and second end 20 are made of at least one member of the group consisting of polyimide, polycarbon, stainless steel, and steel, iron, plastic aluminum, and the like materials.

In a preferred embodiment of disposable tip assembly 10 for reusable surgical laser treatment device 500, the tip assembly 10 is packaged as a sterile assembly and comprises in combination: a first sleeved end 16 adapted to releasably fit on the device 500 and having a longitudinal axis 12; a second cannula end 20 tapering to a discharge tip 22; optical fiber means 30 for delivery of light energy axially positioned within the tip assembly 10 and extending beyond the discharge tip 22; means for removably locking the first sleeved end 16 to the device 500, and connecting the first sleeved end 16, second cannula end 20, and optical fiber means 30; and means for aligning fiber optic means 30 within the tip assembly 10 with reusable device 500 for surgical laser treatment.

Means for aligning the optical fiber means 30 within the tip assembly 10 with the surgical device 500 comprises at least two slits 550 spaced equally apart on the distal end of the surgical device 500 and internal longitudinal ribs 18 on the sleeve 16 adapted to fit the surgical device slits 550. These slits 550 and corresponding ribs 18 are precisely machined to high tolerance in such a manner that the precision of alignment of optical fiber means 30 within the tip assembly 10 with the surgical device 500 is not dependent upon the strength or size of magnetic material in the housing 54 or the surgical device 500. This alignment assembly allows variable rotation of the tip assembly 10 with the surgical device 500 to allow use of the same surgical device 500 device by right- or left-handed surgeons.

For a preferred embodiment of sterile polyimide sleeve assembly 10 for reusable laser surgical device 500, the sleeve assembly comprises in combination: a first end 10 having a longitudinal axis 12 and adapted to releasably fit on a distal end of the surgical device 550; a cannula second end 20 tapering to a discharge tip 22 at an acute downward angle to the first end longitudinal axis 12; optical fiber means 30 for delivery of light energy axially positioned within the tip assembly from within the first end 10 and extending beyond the discharge tip 22; magnetic means 50 for releasably locking the first end to the surgical device distal end and connecting the first end 10, cannula second end 20, and optical fiber means 30; and six slits 550 spaced sixty degrees apart on the distal end of the surgical device 500 and first end internal longitudinal ribs 18 adapted to fit the surgical device slits 550.

We claim:

1. A disposable tip apparatus for a reusable laser surgical device, the tip apparatus comprising in combination: a) a first end having a longitudinal axis and adapted to releasably fit on the distal end of the surgical device; b) a second end tapering to a discharge tip; c) optical fiber means for delivery of light energy axially positioned within the tip apparatus from within the first end and extending beyond the discharge tip; d) means for releasably locking the first end to the surgical device, and connecting the first end, second end, and optical fiber means; and e) means for aligning the optical fiber means within the tip apparatus with the surgical device for surgical laser treatment, wherein the means for aligning comprises a sleeve on the tip first end that includes a plurality of spaced apart longitudinally extending internal ribs adapted to fit corresponding slits on the distal end of the surgical device.

2. The tip apparatus of claim 1, wherein the discharge tip end is along the first end longitudinal axis.

3. The tip apparatus of claim 1, wherein the discharge tip end is at an acute angle to the first end longitudinal axis.

4. The tip apparatus of claim 1, wherein the discharge tip end is at a right angle to the first end longitudinal axis.

5. The tip apparatus of claim 1, wherein means for removably locking the first end to the surgical device comprises at least one member of the group consisting of means for magnetic coupling, means for mechanical coupling, means for electro-mechanical coupling, and means for electro-magnetic coupling.

6. The tip apparatus of claim 1, wherein the tip apparatus is made of at least one member of the group consisting of polyimide, polycarbon, stainless steel, steel, iron, plastic, and aluminum.

7. The tip apparatus of claim 1 packaged as a sterile assembly.

8. A disposable tip assembly for a reusable surgical laser treatment device, the tip assembly comprising in combination: a) a first sleeved end adapted to releasably fit on the device and having a longitudinal axis; b) a cannula second end tapering to a discharge tip; c) optical fiber means for delivery of light energy axially positioned within the tip assembly and extending beyond the discharge tip; d) connecting means for releasably locking the sleeved end to the device and connecting the first sleeved end, cannula second end, and optical fiber means, wherein the connecting means comprises a connector that includes a housing that receives the cannula second end and a probe that is adapted to extend into the surgical device, and wherein the housing and the probe cooperate to define a longitudinal opening through which the optical fiber means extends; and e) means for aligning fiber optic means within the tip assembly with reusable device for surgical laser treatment.

9. The tip assembly of claim 8, wherein means for aligning the optical fiber means within the tip assembly with the surgical device comprises at least two slits spaced equally apart on the distal end of the surgical device and the sleeve end having internal longitudinal ribs adapted to fit the surgical device slits.

10. The tip assembly of claim 8, wherein the discharge tip end is along the sleeve end longitudinal axis.

11. The tip assembly of claim 8, wherein the discharge tip end is at an acute angle to the sleeve end longitudinal axis.

12. The tip assembly of claim 8, wherein the discharge tip end is at a right angle to the sleeve end longitudinal axis.

13. The tip assembly of claim 8, wherein means for removably locking the sleeve end to the surgical device comprises at least one member of the group consisting of means for magnetic coupling, means for mechanical coupling, means for electro-mechanical coupling, and means for electro-magnetic coupling.

14. The tip assembly of claim 8, wherein the tip assembly is made of at least one member of the group consisting of polyimide, polycarbon, stainless steel, steel, iron, plastic, and aluminum.

15. The tip assembly of claim 8 packaged as a sterile assembly.

16. The tip assembly of claim 8 wherein the means for removably locking the sleeve end to the surgical device comprises a magnet disposed in the connector that is adapted to mate with a magnet disposed in the surgical device.

17. Disposable sterile polyimide sleeve assembly for reusable laser surgical device, the sleeve assembly comprising in combination: a) a first end having a longitudinal axis and adapted to releasably fit on a distal end of the surgical device; b) a cannula second end tapering to a discharge tip at an acute downward angle to the first end longitudinal axis; c) optical fiber means for delivery of light energy axially positioned within the tip assembly from within the first end and extending beyond the discharge tip; d) magnetic means for releasably locking the first end to the surgical device distal end, and connecting the first end, cannula second end, and optical fiber means; and e) six slits spaced sixty degrees apart on the distal end of the surgical device and first end internal longitudinal ribs adapted to fit the surgical device slits.

* * * * *